(12) United States Patent  
Yamaguchi et al.

(10) Patent No.: US 11,957,506 B2  
(45) Date of Patent: Apr. 16, 2024

(54) TESTING METHOD FOR DETERMINING ORAL INDICATOR

(71) Applicant: LION CORPORATION, Sumida-ku (JP)

(72) Inventors: Tsuguno Yamaguchi, Tokyo (JP); Shinsuke Kataoka, Tokyo (JP)

(73) Assignee: LION CORPORATION, Sumida-ku (JP)

( * ) Notice: Subject to any disclaimer, the term of this patent is extended or adjusted under 35 U.S.C. 154(b) by 43 days.

(21) Appl. No.: 16/970,702

(22) PCT Filed: Feb. 26, 2019

(86) PCT No.: PCT/JP2019/007367  
§ 371 (c)(1),  
(2) Date: Aug. 18, 2020

(87) PCT Pub. No.: WO2019/167963  
PCT Pub. Date: Sep. 6, 2019

(65) Prior Publication Data  
US 2020/0375570 A1 Dec. 3, 2020

(30) Foreign Application Priority Data  
Mar. 2, 2018 (JP) ................. 2018-037035

(51) Int. Cl.  
*A61B 8/08* (2006.01)  
*A61B 8/12* (2006.01)  
*A61C 19/04* (2006.01)

(52) U.S. Cl.  
CPC .............. *A61B 8/0858* (2013.01); *A61B 8/12* (2013.01); *A61C 19/04* (2013.01)

(58) Field of Classification Search  
None  
See application file for complete search history.

(56) References Cited

U.S. PATENT DOCUMENTS 9,039,621 B2    5/2015  Mukdadi et al.  
2004/0242987 A1*  12/2004  Liew ............... A61B 6/482  
                                          600/407

(Continued)

FOREIGN PATENT DOCUMENTS

DE   10 2015 011 388 A1   3/2017  
JP      2000-5170 A       1/2000

(Continued)

OTHER PUBLICATIONS

Salmon, B., et al., "Intraoral ultrasonography: development of a specific high-frequency probe and clinical pilot study", Clin. Oral. Invest (2012) vol. 16, XP035032290, pp. 643-649.

(Continued)

*Primary Examiner* — Shahdeep Mohammed  
(74) *Attorney, Agent, or Firm* — Oblon, McClelland, Maier & Neustadt, L.L.P.

(57) ABSTRACT

Provided is a testing method for determining an oral indicator by which an oral indicator can be determined. The testing method for determining an oral indicator includes an image acquisition step of acquiring an ultrasonic image of an inside of an attached gingiva of a subject, using a measurement probe, an average brightness acquisition step of acquiring average brightness of the ultrasonic image, and an indicator determination step of determining an oral indicator of the subject by referring to the average brightness and a reference of an oral indicator.

13 Claims, 5 Drawing Sheets

(56) References Cited

U.S. PATENT DOCUMENTS

| | | | |
|---|---|---|---|
| 2004/0260177 A1* | 12/2004 | Simopoulos | G06T 5/50 600/437 |
| 2007/0168152 A1 | 7/2007 | Matov et al. | |
| 2013/0029293 A1 | 1/2013 | Mukdadi et al. | |
| 2014/0005500 A1 | 1/2014 | Cales et al. | |
| 2015/0313572 A1* | 11/2015 | Gerbaulet | A61C 19/04 433/29 |
| 2017/0165040 A1* | 6/2017 | Wolgin | A61M 1/962 |
| 2018/0098728 A1 | 4/2018 | Cales et al. | |

FOREIGN PATENT DOCUMENTS

| | | |
|---|---|---|
| JP | 3040980 B1 | 5/2000 |
| JP | 2001-170087 A | 6/2001 |
| JP | 2006-223676 A | 8/2006 |
| JP | 2013-146469 A | 8/2013 |
| JP | 2014-508936 A | 4/2014 |
| JP | 6119013 B1 | 4/2017 |

OTHER PUBLICATIONS

Fragrance Journal, March 3, 2016, Research & Development for Cosmetics, Toiletries & Allied Industries, 3 pages.

International Search Report dated Apr. 23, 2019 in PCT/JP2019/007367 filed on Feb. 26, 2019, citing documents AQ and AR therein, 1 page.

Office Action in Taiwanese Patent Application No. 108106902 dated Mar. 30, 2023 (Reference 1 is cited therein).

* cited by examiner

TESTING METHOD FOR DETERMINING ORAL INDICATOR

FIELD

The present invention relates to a testing method for determining an oral indicator.

BACKGROUND

Maintaining and improving a health state in the oral cavity is extremely important in an aesthetic point of view and in view of disease prevention. Specifically, normalizing the constituents in the oral tissue as appropriate and making the gum healthy from the inside are important not only in view of oral appearance that is an aesthetic point of view but also in view of disease prevention.

Conventionally, oral clinical indicators (gingiva health state) are diagnosed by dentists, for example, by means of pocket probing or X-ray examination, which is not an easy or quantitative method for evaluating a gingival health state. Consequently, lack of realization of the efficacy of gum care leads to reducing motivation and hinders selection of gum care suitable for each individual.

In view of the problem above, the methods of objectively evaluating a gingival state have been examined (for example, see Patent Literatures 1 to 2).

CITATION LIST

Patent Literature

Patent Literature 1: Japanese Patent Application Laid-open No. 2001-170087
Patent Literature 2: Japanese Patent No. 3040980

SUMMARY

Technical Problem

Figure 3:
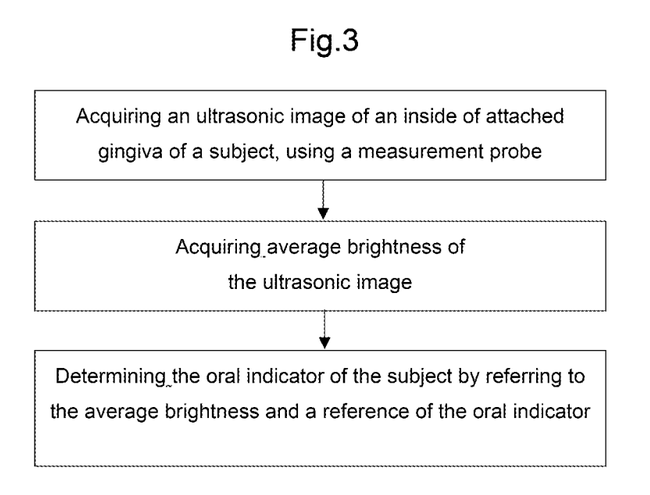
FIG. 3 is a flow diagram illustrating an aspect of the invention.
Figure 4:
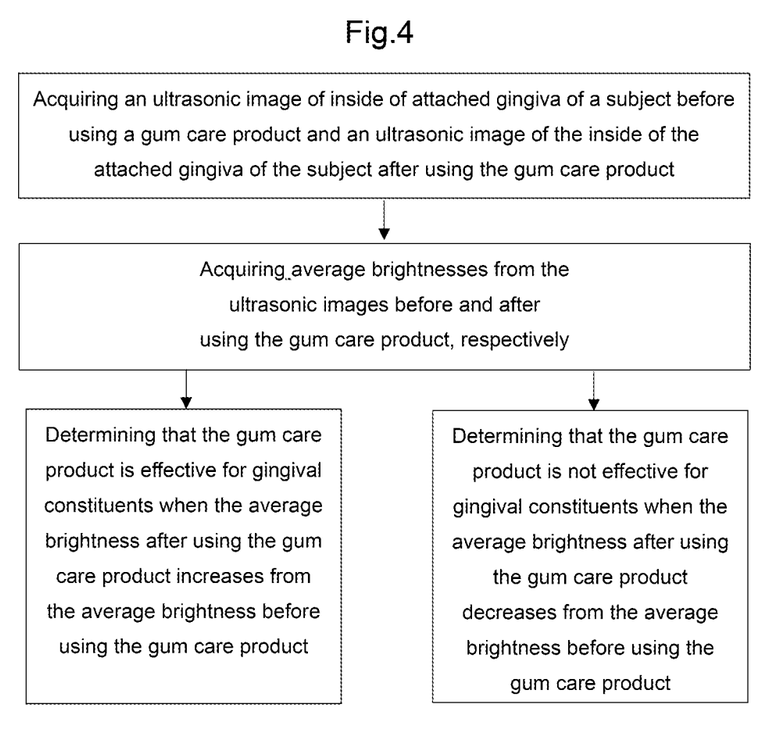
FIG. 4 is a flow diagram illustrating an aspect of the invention.
Figure 5:
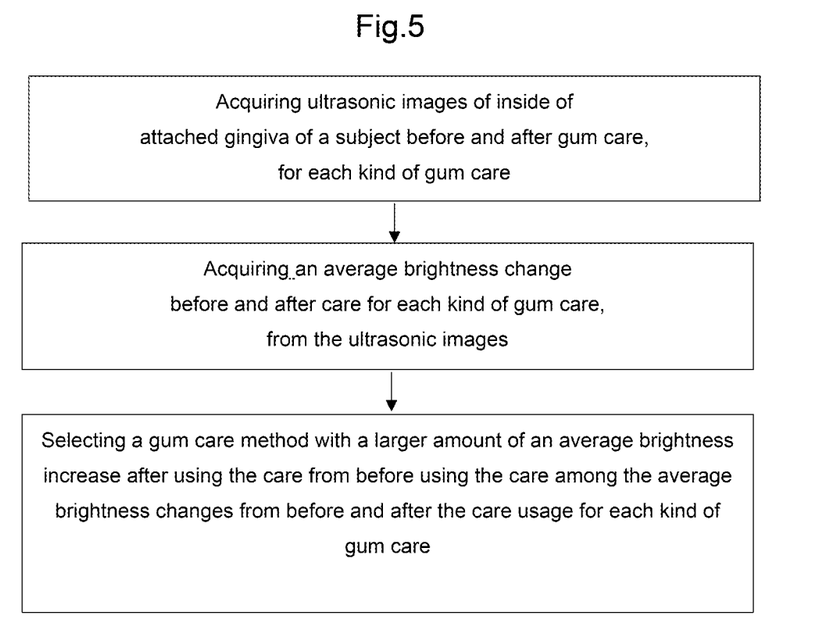
FIG. 5 is a flow diagram illustrating an aspect of the invention.
Figure 6:
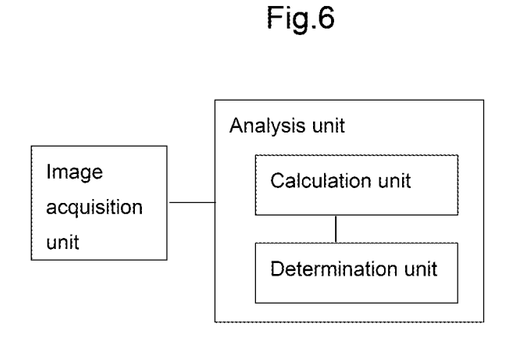
FIG. 6 is a flow diagram illustrating an aspect of the invention.

In the method in Patent Literature 1, the measurement is complicated and takes time, with a large measurement error. FIG. 3 illustrates that the $R^2$ value is about 0.5 and the error is large. The method in Patent Literature 2 provides an indicator for oral appearance but does not provide an indicator for the constituents in the oral tissue, such as the collagen content. Development of other methods have been sought for as a method of evaluating an oral clinical indicator (gingival health state).

Indicators indicating the internal structure of gingiva or information on its change related to aging and diseases are unknown. Specific problems in the method of evaluating an oral clinical indicator (gingival health state) include the following two points.

(1) Construction of evaluation and measurement methods for oral clinical indicators (2) Estimation of age, health state, and disease from oral clinical indicators The problem of the present invention is to provide a testing method for determining an oral indicator (gingival health state) by which an oral indicator can be determined.

Solution to Problem

The inventors of the present invention have conducted elaborate studies on the problem above and found that the problem above can be solved by using the average brightness in a region inside the attached gingiva of a subject obtained from an ultrasonic image. This finding has led to completion of the invention.

Specifically, the inventors of the invention provide the following [1] to [18].

[1] A testing method for determining an oral indicator, the testing method comprising: an image acquisition step of acquiring an ultrasonic image of an inside of an attached gingiva of a subject, using a measurement probe; an average brightness acquisition step of acquiring average brightness of the ultrasonic image; and an indicator determination step of determining an oral indicator of the subject by referring to the average brightness and a reference of an oral indicator.

[2] The testing method according to [1], wherein a tip end of the measurement probe for measuring a surface of the attached gingiva has a diameter of 0.1 to 5 mm.

[3] The testing method according to [1] or [2], wherein a region of the inside of the attached gingiva of which the ultrasonic image is acquired is at least a part of a range from immediately below epithelium to 1500 μm below epithelium-connective tissue border.

[4] The testing method according to any one of [1] to [3], wherein an acquisition range of the ultrasonic image has an area equal to or smaller than 20 mm$^2$.

[5] The testing method according to any one of [1] to [4], wherein the image acquisition step is a step of acquiring the ultrasonic image with ultrasound having a radiation wavelength of 10 to 50 MHz.

[6] The testing method according to any one of [1] to [5], wherein the reference is previously-acquired average brightness associated with an oral indicator.

[7] The testing method according to [6], wherein the indicator determination step is a step of determining that the amount of gingival collagen is high, the gingival age is young, the all teeth average pocket depth is shallow, the mobility of adjacent teeth is low, the bleeding on probing (BOP) positive ratio is low, the periodontal inflamed surface area (PISA) is small, or the periodontal epithelial surface area (PESA) is small when the average brightness of the subject is higher than a reference value that is the previously-acquired average brightness associated with the oral indicator.

[8] The testing method according to [6], wherein the indicator determination step is a step of determining that the amount of gingival collagen is low, the gingival age is old, the all teeth average pocket depth is deep, the mobility of adjacent teeth is high, the bleeding on probing (BOP) positive ratio is high, the periodontal inflamed surface area (PISA) is large, or the periodontal epithelial surface area (PESA) is large when the average brightness of the subject is lower than a reference value that is the previously-acquired average brightness associated with the oral indicator.

[9] The testing method according to any one of [1] to [5], wherein the reference is a statistical regression formula of an oral indicator.

[10] A method of evaluating a gum care product, the method comprising: using a measurement probe, acquiring an ultrasonic image of the inside of attached gingiva of a subject before using a gum care product and an ultrasonic image of the inside of the attached gingiva of the subject after using the gum care product; acquiring average brightnesses from the ultrasonic images before and after using the gum care product, respectively; and determining that the gum care product is effective for gingival constituents when the average brightness after using the gum care product increases from the average brightness before using the gum care product, and determining that the gum care product is not effective for gingival constituents when the average brightness after using the gum care product decreases from the average brightness before using the gum care product.

[11] A method of selecting a gum care method, the method comprising: using a measurement probe, acquiring ultrasonic images of an inside of an attached gingiva of a subject before and after gum care, for each kind of gum care; acquiring an average brightness change before and after care for each kind of gum care, from the ultrasonic images; and selecting a gum care method with a large increase of average brightness after the care compared to before the care among the average brightness changes between before and after care for each kind of gum care.

[12] An oral indicator determining device comprising: an image acquisition unit configured to acquire an ultrasonic image of inside of an attached gingiva of a subject, using a measurement probe; and an analysis unit configured to analyze the ultrasonic image, the analysis unit including a calculation unit configured to calculate average brightness of the inside of the attached gingiva from the ultrasonic image, and a determination unit configured to determine an oral indicator by referring to the average brightness and a reference of an oral indicator.

[13] The oral indicator determining device according to [12], wherein a tip end of the measurement probe for measuring the attached gingiva has a diameter of 0.1 to 5 mm.

[14] The oral indicator determining device according to [12] or [13], wherein the ultrasonic image is acquired with ultrasound having a radiation wavelength of 10 to 50 MHz.

[15] The oral indicator determining device according to any one of [12] to [14], wherein the reference is previously-acquired average brightness associated with an oral indicator.

[16] The oral indicator determining device according to [15], wherein the determination unit configured to determine that the amount of gingival collagen is high, the gingival age is young, the all teeth average pocket depth is shallow, the mobility of adjacent teeth is low, the bleeding on probing (BOP) positive ratio is low, the periodontal inflamed surface area (PISA) is small, or the periodontal epithelial surface area (PESA) is small when the average brightness of the subject is higher than a reference value that is the previously-acquired average brightness associated with the oral indicator.

[17] The oral indicator determining device according to [15], wherein determination unit configured to determine that the amount of gingival collagen is small, the gingival age is old, the all teeth average pocket depth is deep, the mobility of adjacent teeth is high, the bleeding on probing (BOP) positive ratio is high, the periodontal inflamed surface area (PISA) is large, or the periodontal epithelial surface area (PESA) is large when the average brightness of the subject is smaller than a reference value that is the previously-acquired average brightness associated with the oral indicator.

[18] The oral indicator determining device according to any one of [12] to [14], wherein the reference is a statistical regression formula of an oral indicator.

Advantageous Effects of Invention

The present invention provides a testing method for determining an oral indicator (gingival health state) by which an oral indicator can be determined.

DESCRIPTION OF EMBODIMENTS

The present invention will be described in detail below in conjunction with preferred embodiments thereof.

In the present disclosure, "determination (evaluation, estimation)" refers to a qualitative or quantitative determination made preliminarily to a diagnosis in medical practice usually by doctors.

[1. Testing Method for Determining Oral Indicator]

A testing method for determining an oral indicator in the present invention includes an image acquisition step of acquiring an ultrasonic image of the inside of the attached gingiva of a subject, using a measurement probe, an average brightness acquisition step of acquiring average brightness of the ultrasonic image, and an indicator determination step of determining an oral indicator of the subject by referring to the average brightness and a reference of an oral indicator.

The testing method in the present invention has been completed by the finding that only the average brightness in a region within the attached gingiva in the gingiva has a correlation with the oral indicator, in a variety of studies by the inventors of the present invention.

It is known that the amount of collagen is correlated with the brightness obtained by ultrasonic analysis, and this correlation is used to analyze, for example, skin age in the field of dermatology. This is based on the knowledge that bare skin exposed to UV suffers damage of collagen and the amount of collagen in skin generally decreases with aging.

However, there has been no study on the correlation of the amount of gingival collagen with oral age. The reason for this is presumably that the oral cavity is hardly exposed to UV in daily life and, in general, it is not easy to estimate a decrease in amount of gingival collagen with aging.

The testing method in the present invention is based on the finding hardly conceivable even by those skilled in the art that only the average brightness of a region inside the attached gingiva is correlated with an oral indicator such as the amount of gingival collagen as described above.

[1-1. Image Acquisition Step]

The image acquisition step is a step of acquiring an ultrasonic image of the inside of the attached gingiva of a subject, using a measurement probe.

When ultrasound is applied to a surface of the attached gingiva of a subject, ultrasound is reflected by the structure inside the attached gingiva and returns to the surface of the attached gingiva of the subject. The reflected ultrasound is influenced by the structure inside the attached gingiva. The ultrasonic analysis is therefore a technique providing structure information inside the attached gingiva of the subject.

In general, ultrasound refers to sound waves having a frequency equal to or higher than 20 kHz. When ultrasound having a long wavelength is applied, ultrasound can reach as far as connective tissue containing collagen, deeper than the epithelium, and can image even the alveolar bone surface. On the other hand, radiation of excessively long wavelengths is not preferable since it is necessary to view a shallow portion immediately below the gingival epithelium too. In the testing method in the present invention, therefore, it is preferable to apply ultrasound in a frequency band of preferably 10 to 80 MHz, more preferably 10 to 50 MHz, and further preferably 15 to 25 MHz.

The measurement probe is a part applied to an attached gingiva measurement site of a subject to transmit ultrasound and receive ultrasound reflected from the inside of the attached gingiva of the subject. When an ultrasonic image is measured, a protective film may be interposed between the measurement probe and the attached gingiva measurement site of the subject. In order to measure only the attached gingiva portion and to measure a range as large as possible to reduce variations, the diameter of the tip end of the measurement probe for measuring the surface of the attached gingiva of the subject is preferably 0.1 to 5 mm, more preferably 0.3 to 4 mm, and further preferably 0.5 to 3 mm.

When the diameter of the tip end of the measurement probe for measuring the surface of the attached gingiva of the subject is 5 mm or less, the correlation with an oral indicator is high. On the other hand, with 0.1 mm or greater, the effect of the structure such as blood vessels in the gingiva is reduced and the reproducibility is high. The shape of the tip end of the measurement probe is not necessarily a circle. For example, an oval, quadrature, or square shape may be employed.

In the present disclosure, "diameter" refers to the diameter of a circle when the shape of the tip end of the probe is a pure circle, and refers to the shorter diameter of an oval when the shape of the tip end of the probe is an oval. When the shape of the tip end of the probe is a rectangle, the diameter refers to the length of the short side, and when it is a square, the diameter refers to the length of one side.

When the shape of the tip end of the probe is an oval, the longer diameter may be 5 mm or greater. When the shape of the tip end of the probe is a rectangle, the length of the long side may be 5 mm or greater.

Examples of the measurement probe include a measurement probe that can be connected to and can transfer information to the analysis unit, and a measurement probe that can be connected to and can transfer information to a communication device such as a smartphone, a mobile phone, and a personal computer.

Gingiva is mainly classified into attached gingiva and alveolar mucosa. They are divided by the mucogingival junction that can be visually identified. The area closer to the teeth with respect to the mucogingival junction is referred to as attached gingiva. The attached gingiva attaches to the alveolar bone and the cementum by fibers in the gingiva. On the other hand, the alveolar mucosa is not bonded to the interior hard tissue.

The thickness of the gingiva varies from person to person. It is therefore preferable to define an analysis range by the distance from the epithelium. The region inside the attached gingiva from which an image is acquired is preferably at least a part of the range from immediately below the epithelium to 1500 μm below the epithelium, more preferably at least a part of the range from immediately below the epithelium to 1000 μm below the epithelium, and further preferably at least a part of the range from immediately below the epithelium to 800 μm below the epithelium.

When the range from immediately below the epithelium up to 1500 μm below the epithelium is analyzed, the alveolar bone existing deeper than this region is avoided, and the quantitative value (brightness) does not include anything other than connective tissue, thereby improving the reliability of measurement values. When the range from immediately below the epithelium up to 800 μm below the epithelium is analyzed, a region with less collagen falls outside the analysis region and a region with much collagen is sufficiently covered, thereby reducing variations and improving the reliability of measurement values.

As described above, gingiva is mainly classified into attached gingiva and alveolar mucosa. The average brightness of the inside of the alveolar mucosa is not found to be correlated with the oral indicator, and only the average brightness of the inside of the attached gingiva is correlated with the oral indicator. The measurement site is the attached gingiva. However, for easiness of measurement, high reproducibility of measurement values, and high correlation to the oral indicator, the measurement site in the attached gingiva is preferably the maxillary attached gingiva, more preferably the attached gingiva of Upper #1 to #5, and further preferably the attached gingiva at three points between Upper Left/Right #1 and #2 and between Upper Right #1 and Upper Left #1.

The reproducibility of measurement values is higher in the maxillary gingiva compared with the mandible and at Upper #1 to #5 compared with the molars. The three points between Upper Left/Right #1 and #2 and between Upper Right #1 and Upper Left #1 have a high correlation with the oral indicator.

The ultrasonic image can be captured as it is as image data into the analysis unit (software) to be used for image analysis, or the ultrasonic image may be printed and captured through, for example, an image scanner to be used for image analysis. It is important that the analysis has a sufficient resolution. As used herein "sufficient resolution" refers to such a degree that the boundary between the epithelium and the connective tissue is clearly distinguishable.

In order to measure only a certain portion of the attached gingiva and to measure a range as large as possible in the portion to reduce variations, the image acquisition range preferably has an area of 20 mm$^2$ or smaller. The image acquisition range is preferably 0.01 to 20 mm$^2$, more preferably 0.09 to 16 mm$^2$, and further preferably 0.25 to 9 mm$^2$. The image may have a shape other than a circle.

When the image acquisition range is 20 mm$^2$ or smaller, the correlation with the oral indicator is even higher. On the other hand, when it is 0.01 mm$^2$ or greater, the effect of the structure such as blood vessels in the gingiva is reduced and the reproducibility is high.

[1-2. Average Brightness Acquisition Step]

The average brightness acquisition step is a step of acquiring the average brightness of the ultrasonic image acquired as described above.

The average brightness can be acquired, for example, by selecting a region to be analyzed in the ultrasonic image and calculating the average value in the area using software (for example, image processing software "Image")). The average brightness in the entire analysis target area can be calculated by selecting a plurality of narrow areas in the region to be analyzed and statistically analyzing their individual average values. The function of calculating the average brightness is often installed in the software of the analysis unit and can be easily obtained. Even when the function is not installed in the software, the average brightness in the analysis target region can be calculated by measuring the brightness at sufficient points.

[1-3. Indicator Determination Step]

The indicator determination step is a step of determining an oral indicator of the subject by referring to the average brightness and a reference of an oral indicator.

As used herein "oral indicator" refers to an indicator related to the state or symptom of the oral cavity, more specifically refers to an indicator concerning the morphology, physical properties, state, etc. of the oral cavity. Examples include the all teeth average pocket depth, the amount of gingival collagen, the gingival age representing the aging state of the gingiva, an indicator related to the state and/or symptom of the gingiva, such as tooth mobility, the bleeding on probing (BOP) positive ratio, periodontal inflamed surface area (PISA), and periodontal epithelial surface area (PESA).

The reference of an oral indicator may be the previously-acquired average brightness at least associated with the oral indicator. The oral indicator thus can be determined qualitatively by comparing the average brightness of the subject with a reference. For the qualitative determination, for example, when it is higher than the reference, it can be determined that the amount of gingival collagen is high, the gingival age is young, the all teeth average pocket depth is shallow, the mobility of adjacent teeth is low, the bleeding on probing (BOP) positive ratio is low, the periodontal inflamed surface area (PISA) is small, or the periodontal epithelial surface area (PESA) is small.

The previously-acquired average brightness may be a specific numerical value or numerical range. The previously-acquired average brightness being "at least associated with the oral indicator" means that, for example, it is determined in advance that average brightness A (specific numerical value) (for example, equal to or greater than A, equal to or less than A, exceeding A, or less than A) is a reference by which the oral indicator is good or poor. As another example, it means that it is determined in advance that average brightness B to C (specific numerical range) (for example, within the range of B to C or outside the range) is a reference by which the oral indicator is good or poor.

The already-acquired average brightness may be associated with health information in addition to an oral indicator. With this, the already-acquired average brightness associated with another information in which health information is matched with or closest to the subject can be selected as a reference, thereby enabling determination with a higher accuracy. Examples of the health information include smoking history, age group, age, height, weight, and a combination of two or more selected from these, and preferably, at least smoking history and age group are included. In the case of a combination of two or more, it is preferable to set the priorities as to which health information precedes. The health information of a measurement target person in obtaining the already-acquired average brightness (when there are a plurality of measurement target persons, their average value) may be recorded as it is as health information.

A population of a plurality of, preferably 10 or more, and more preferably 20 or more, already-acquired average brightness associated with an oral indicator and preferably with health information may be prepared in advance prior to the determination step. With this, the already-acquired average brightness appropriate as a reference of an oral indicator can be selected as appropriate from the population.

When the reference is a statistical regression formula of an oral indicator, the oral indicator can be determined quantitatively by substituting the average brightness of the subject into the statistical regression formula. With the quantitative determination done in this way, a deviation between the gingival age and the actual age and/or the effect of the difference in daily life caused by smoking, etc. on the oral indicator can be evaluated.

The statistical regression formula can be calculated from a population to such an extent that the effect of individual differences can be ignored. In doing so, the population can be changed according to smoking history, gender, or age. However, since a statistical value need to be set, a population preferably includes at least 20 persons. For accuracy in the quantitative determination, a population preferably includes a larger number of persons.

A case where an oral indicator is determined quantitatively will be described below.

The inventors of the present invention have found that only the average brightness of the inside of the attached gingiva in the gingiva exhibits a certain statistical correlation with an oral indicator. Specifically, according to a population to such an extent that the effect of individual differences can be ignored, the average brightness inside the attached gingiva exhibits a correlation with the oral indicator. The statistical regression formula that may serve as a reference of an oral indicator can be derived using the average brightness as a variable. The correlation analysis can be calculated, for example, using statistical analysis software (for example, "Pharmaco Basic" manufactured by Scientist Press Co., Ltd.) according to the Spearman method, and the calculation of the regression formula can also be conducted, for example, using statistical analysis software.

As one of the modes for quantitatively determining an oral indicator, it is necessary to obtain a statistical regression formula for the oral indicator in advance from a population to such an extent that the effect of individual differences can be ignored. When a statistical regression formula related to the oral indicator is obtained, the conditions of measurement performed for determining the oral indicator of the subject are set to be identical to the conditions of measurement performed for the population. Specifically, the kind of the ultrasonic measurement device, the kind of the measurement probe, the wavelength of ultrasound applied, the sensitivity of the detector, the measurement site in the attached gingiva of the subject are set to be identical. This setting prevents variation in measurement due to the difference in conditions and enables accurate determination of the oral indicator.

It is preferable that the condition for acquiring the average brightness in obtaining a reference for the oral indicator is identical. However, even when the condition for acquiring the average brightness is different, as long as a conversion factor is acquired, the acquisition condition may be different. For example, average brightness may be acquired under a plurality of measurement conditions for the same individual, and the conversion factor as described above may be acquired from the relation between the measurement conditions and the average brightness.

As another mode for quantitatively determining an oral indicator, the oral indicator may be determined by referring to a database of the previously-acquired average brightness associated with the oral indicator and the health information prepared prior to the determination step (for example, selection of a reference, comparison between the average brightness and the reference of an oral indicator, determination of the oral indicator of the subject). The determination step above may be performed by an algorithm based on machine learning.

(Oral Indicator)

The oral indicator is an indicator of the state and/or symptom of the oral cavity, preferably an indicator related to the state and/or symptom of periodontium. In this way, various symptoms in the oral cavity and the possibility of being affected by diseases can be determined using the indicator related to the state and/or symptom of periodontium. Examples of such symptoms and diseases include periodontitis, gingivitis, alveolar pyorrhea, inflammation due to implant failure, thin gingiva, gingival recession, gingival bleeding, gingival color, bad breath, tooth movement, inflammation involved with tooth fracture, root lesion, and fistula formation.

Embodiments using the indicator related to the state and/or symptom of periodontium include estimation of the value of the all teeth average pocket depth, estimation of the bleeding on probing (BOP) positive ratio, estimation of the periodontal inflamed surface area (PISA), and determination of the periodontal epithelial surface area (PESA).

The periodontal pocket depth refers to the depth of the gap between tooth and gingiva. The periodontal pocket depth is usually measured by a dentist, for example, using a special probe by the six-point method and is used for analysis of periodontitis. In the estimation method in the present invention, the all teeth average pocket depth is calculated as the average value of the periodontal pocket depths of all the teeth. All of estimation of the value of the all teeth average pocket depth, estimation of the bleeding on probing (BOP) positive ratio, estimation of the periodontal inflamed surface area (PISA), and estimation of periodontal epithelial surface area (PESA) can be expected to be applied to a preliminary determination as to whether a subject is affected by periodontitis or is likely to be affected.

When used in this embodiment, a reference or a statistical regression formula is preferably obtained from a wide range of targets, irrespective of smoking history, gender, and age group.

Another embodiment using the indicator related to the state and/or symptom of periodontium is determination of the amount of gingival collagen.

Connective tissue is not only mere mechanical supporting tissue but also a tissue having the function of transmitting nutrients, electrolyte, and hormones, and acting as their buffer, or serving as a site of inflammation, immunity, and healing. Collagen is the main constituent of connective tissue and plays physiologically and pathologically important roles, and grasping the amount thereof contributes to prevention of diseases.

When used in this embodiment, a reference or a statistical regression formula is preferably obtained from a wide range of targets, irrespective of smoking history, gender, and age group.

Yet another embodiment using the indicator related to the state and/or symptom of periodontium is determination of gingival age.

The gingival age means the physiological aging state of gingival tissue for each individual and refers to an indicator of the degree of physiological change due to aging of each individual oral cavity. The gingival age does not always have a correlation with the biological age (actual age).

When used in this embodiment, a reference or a statistical regression formula is preferably obtained from a wide range of targets, irrespective of smoking history, gender, and age group.

Yet another embodiment using the indicator related to the state and/or symptom of periodontium is determination of mobility of adjacent teeth.

Movement of teeth means the degree of the teeth mobility due to looseness. The conventional measurement method, such as examining looseness by percussion of teeth, may give the subject pain. The estimation method in the present invention is advantageous in that it can significantly alleviate the burden on the subject in that this measurement can be done merely by applying a probe to the gingival and does not give pain, unlike percussion of teeth.

When used in this embodiment, a reference or a statistical regression formula is preferably obtained from a wide range of targets, irrespective of smoking history, gender, and age group. The mobility of adjacent teeth is preferably at the average brightness measurement site.

[2. Method of Evaluating Gum Care Product]

A method of evaluating a gum care product in the present invention is a method of evaluating a gum care product for gingival constituents. The method of evaluating a gum care product in the present invention can be used for determining the improving effect of using the existing gum care product on the periodontium of a user, developing new gum care products, and determining the usefulness.

The "gum care product" in the present invention is the concept encompassing not only product forms such as toothpaste but also products for caring the gingiva, such as compositions for oral cavity such as mouthwash and liniment (cosmetic products, quasi-drugs, drugs) and oral cleaning tools such as toothbrushes and dental floss.

The method of evaluating a gum care product in the present invention is a method involving: using a measurement probe, acquiring an ultrasonic image of the inside of the attached gingiva of a subject before using a gum care product and an ultrasonic image of the inside of the attached gingiva of the subject after using the gum care product; acquiring average brightnesses from the ultrasonic images before and after using the gum care product, respectively; and determining that the gum care product is effective for gingival constituents when the average brightness after using the gum care product increases from the average brightness before using the gum care product. The method of evaluating a gum care product in the present invention is a method involving: acquiring average brightnesses from the ultrasonic images before and after using the gum care product, respectively as described above; and determining that the gum care product is not effective for gingival constituents when the average brightness after using the gum care product decreases from the average brightness before using the gum care product.

The method of evaluating a gum care product in the present invention is a method of evaluating a gum care product for a gingival constituent by comparing the average brightness of a region inside the attached gingiva between before and after using the gum care product, because the average brightness in a region inside the attached gingiva has a correlation with the oral indicator as described in [1. Testing Method for Determining Oral Indicator].

The other detail including the methods of acquiring the ultrasonic image and the average brightness is similar to the detail described in [1. Testing Method for Determining Oral Indicator].

[3. Method of Selecting Gum Care Method]

A method of selecting a gum care method in the present invention can be used for determining a method suitable for a target from among existing gum care methods, developing new gum care methods, and determining the usefulness.

The method of selecting a gum care method in the present invention is a method of selecting a gum care method involving: using a measurement probe, acquiring ultrasonic images of the inside of the attached gingiva of a subject before and after gum care, for each kind of gum care; acquiring an average brightness change before and after care, for each kind of gum care; and selecting a gum care method with a large amount of average brightness increase among the average brightness changes before and after care for each kind of gum care.

The method of selecting a gum care method is a method of selecting a gum care method with a high average brightness increase by comparing the amount of average brightness increase in a region inside the attached gingiva between before and after gum care, because the average brightness in a region inside the attached gingiva has a correlation with the oral indicator as described in [1. Testing Method for Determining Oral Indicator].

The other detail including the methods of acquiring the ultrasonic image and the average brightness is similar to the detail described in [1. Testing Method for Determining Oral Indicator].

The gum care selected by the present method encompasses methods of caring the gingival and active ingredients useful for care, such as compositions for oral cavity such as toothpaste, mouthwash, and liniment, and oral cleaning tools such as toothbrushes and dental floss.

[4. Oral Indicator Determining Device]

An oral indicator determining device in the present invention includes an image acquisition unit configured to acquire an ultrasonic image of the inside of the attached gingiva of a subject, using a measurement probe, and an analysis unit configured to analyze the ultrasonic image. The analysis unit includes a calculation unit configured to calculate average brightness of the inside of the attached gingiva from the ultrasonic image acquired by the image acquisition unit and a determination unit configured to determine an oral indicator by referring to the average brightness and a reference of an oral indicator.

The oral indicator determining device in the present invention includes an image acquisition unit and an analysis unit and includes the one having those units in one piece. The detail of the image acquisition unit is similar to the detail described in [1-1. Image Acquisition Step] in [1. Testing Method for Determining Oral Indicator].

The analysis unit includes a calculation unit configured to calculate average brightness and a determination unit configured to determine an oral indicator. The detail of the calculation unit is similar to the detail described in [1-2. Average Brightness Acquisition Step] in [1. Testing Method for Determining Oral Indicator]. The determination unit is similar to the one described in [1-3. Indicator Determination Step] in [1. Testing Method for Determining Oral Indicator].

The calculation unit and the determination unit may be performed in the same device or may be performed in different devices.

EXAMPLES

The present invention will be described in more detail below with examples. The following examples are provided for describing the present invention suitably and are not intended to limit the present invention. In the analysis, an ultrasonic dermal image device "DermaLab" (manufactured by Cortex Technology) was used, and a circular probe (manufactured by Integral Cooperation) having a tip end with a diameter of 2 mm was used as a probe in contact with a test site, unless otherwise specified.

Reference Example 1: Imaging of Gingival Collagen

For a plurality of points in guinea pig gingiva, an ultrasonic image was acquired using DermaLab. Subsequently, the site was thinly sliced and stained by Masson's trichrome stain (manufactured by Sigma-Aldrich) for collagen staining. In the stained image, only a blue portion was extracted and digitized into an image A. The ultrasonic image and the image A were each divided into 50-μm square grids, and the average brightness of each grid was calculated for all the grids in both images.

The corresponding grids in the ultrasonic image and the image A were determined based on the position of epithelium and muscle, and the correlation between the average brightness in the ultrasonic image and the average brightness in the image A in the corresponding grids was analyzed. As a result, it was found that the average brightness in the ultrasonic image and the image A has a significant correlation at a significance level of less than 1%, that is, the average brightness in the ultrasonic image has a correlation with the amount of collagen. This result has demonstrated that imaging of collagen was correctly performed in the ultrasonic image analysis.

Example 1 and Comparative Example 1:
Correlation Between Subject Age Group and
Average Brightness of Ultrasonic Image
(Determination of Gingival Age)

For 109 men and women between the age of 24 to 64, ultrasonic images of the gingiva were acquired and subjected to image analysis to calculate the average brightness of connective tissue.

Gingival ultrasonic images were taken as follows. A probe with a drop of gel made of an edible component was applied to attached gingiva region about 3 mm from the gingival margin in the interdental papilla of Upper Left/Right #1 to #5 or an alveolar mucosa region above the mucogingival junction about 1 cm above the attached gingiva region to emit ultrasound of 20 MHz and receive the reflected wave. The reflected wave was converted into an image by a computer and stored as an ultrasonic image. This image was analyzed using common image analysis software (ImageJ (the National Institutes of Health)), and the average brightness of the connective tissue in a range from immediately below the epithelium to 500 μm below the epithelium in the ultrasonic image was calculated. For each subject, a total of nine points described above were measured three times per site, and the value obtained by averaging a total of 27 pieces of data was considered as the average brightness of the subject. The values calculated for each age group of subjects were averaged, and the correlation with the group age was analyzed. The analysis result of the attached gingiva is illustrated in FIG. 1, and the analysis result of the alveolar mucosa is illustrated in FIG. 2.

Figure 1:
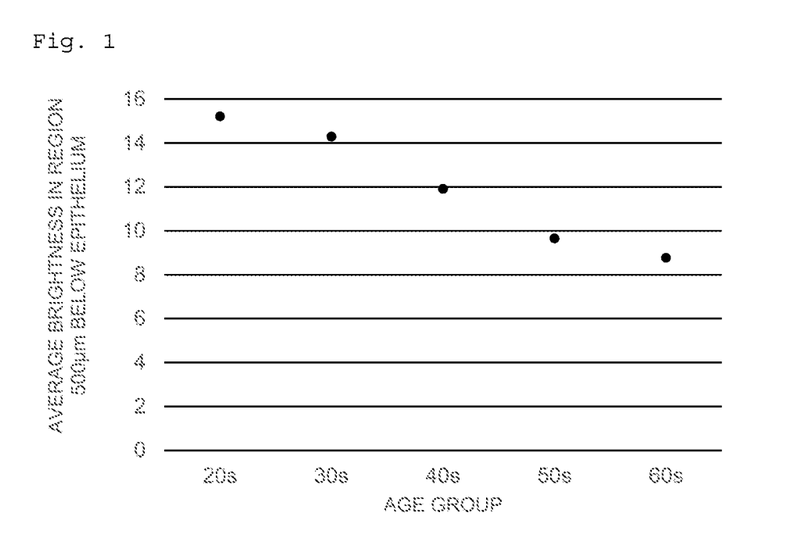
FIG. 1 is a graph illustrating the correlation of the average value of average brightness inside the attached gingiva with subject age groups.
Figure 2:
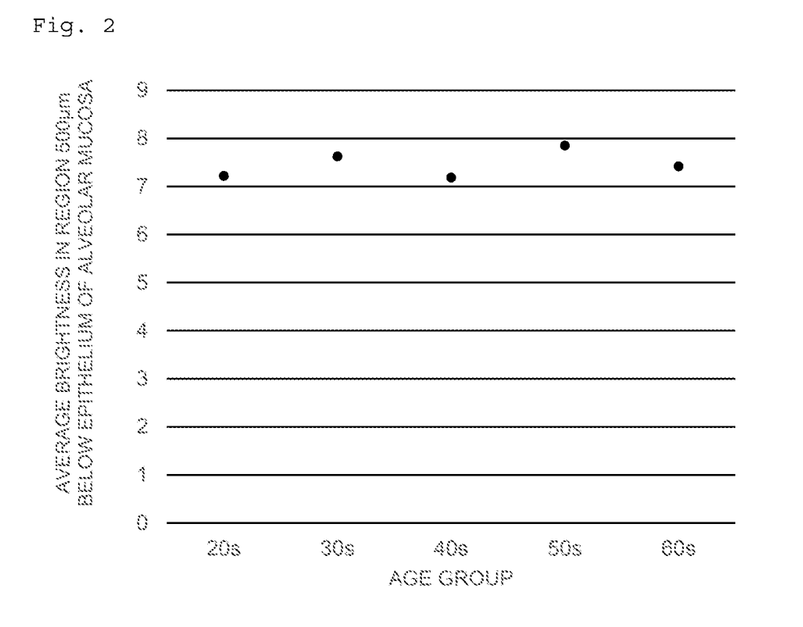
FIG. 2 is a graph illustrating the correlation of the average value of average brightness inside the alveolar mucosa with subject age groups.

The analysis result illustrated in FIG. 1 indicates that the average brightness representing the amount of gingival collagen in the attached gingiva has a negative correlation with the subject age groups at a significance level of less than 5%. The analysis result illustrated in FIG. 2 indicates that the average brightness representing the amount of gingival collagen in the alveolar mucosa has no correlation with the subject age groups.

Based on the results above, the gingival age of a subject, that is, the physiological aging state of each individual gingiva can be determined by measuring the average brightness of an ultrasonic image of the attached gingiva area of a subject and substituting the average brightness into a statistically derived statistical regression formula of the average brightness of an ultrasonic image of the attached gingiva area and the subject age group.

For example, in this analysis result, the regression formula (18.97−"the average brightness in a range from immediately below the epithelium to 500 μm below the epithelium")÷0.175="gingival age" was statistically obtained.

With this, the gingival health state of the subject can be determined from the deviation between the actual age and the gingival age and applied to selection of an oral care agent and an oral care method suitable for the subject and oral aesthetics aiming to improve aesthetic properties by rejuvenation of the gingival state.

Example 2: Correlation of Average Brightness of Ultrasonic Image to Subject Age Group and Smoking History (Determination of Gingival Health State)

Forty-four men between the age of 50 to 64 were divided into two groups according to smoking history through a questionnaire. Sixteen people had smoking history and 28 people had no smoking history. The average age of the subjects in both groups was almost the same: 53.2 years old for those with smoking history and 53.5 years old for those with no smoking history.

For each subject, the average brightness was calculated at all of 27 measurement sites in a range from immediately below the gingival epithelium to 500 μm below the epithelium, by the method in Example 1. The average value of the average brightness of the subjects in the group with smoking history is 9.0, whereas the average value of the average brightness of the subjects in the group with no smoking history is 10.0.

The regression formula statistically obtained in this analysis is:

gingival age=107.5−5.5×average brightness.

The average brightness of each group is substituted into the formula to yield the gingival age of 58 for the subject group with smoking history and 52.5 for the group with no smoking history.

It is commonly estimated that oxidant stress of smoking causes decomposition of gingival collagen, and presumably, the amount of gingival collagen of a subject with smoking history is smaller than the amount of gingival collagen of a subject with no smoking history. In other words, according to the above result, it can be said that the average brightness of an ultrasonic image of the attached gingiva area is data demonstrating that the gingival age changes not only with the actual age but also with a factor that may influence the amount of collagen. Thus, the gingival age of a subject can be determined by measuring the average brightness of an ultrasonic image of the attached gingiva area of the subject and substituting the average brightness into a statistically derived statistical regression formula of the average brightness of an ultrasonic image of the attached gingiva area and the subject age. The gingival age of the subject can also be estimated by comparing the average brightness of the subject with the average brightness of which relation with the gingival age is known. The gingival health state of the subject therefore can be determined from the deviation between the gingival age and the actual age of the subject and applied to fitting oral aesthetics.

Example 3: Correlation Between all Teeth Average Pocket Depth (Mm) of Subject and Average Brightness of Ultrasonic Image (Determination of the Value of all Teeth Average Pocket Depth)

For 40 men between the age of 55 to 60, one dental hygienist measured the periodontal pocket depths of all the teeth by the six-point method and calculated the all teeth average pocket depth of each subject.

For each subject, the average brightness of connective tissue in the attached gingiva of the interdental papilla of Upper Left/Right #1 to #5 was calculated by the method in Example 1. The correlation between the all teeth average periodontal pocket depth calculated by the dental hygienist and the average brightness of the ultrasonic image of the attached gingiva in the ranges from immediately below the epithelium to 500 μm below the epithelium and from immediately below the epithelium to 1500 μm below the epithelium was analyzed. The analysis result is illustrated in Table 1 below.

TABLE 1

| All teeth average pocket depth | Average brightness of attached gingiva | |
|---|---|---|
| | From immediately below epithelium to 500 μm below epithelium | From immediately below epithelium to 1500 μm below epithelium |
| 5 mm or more | 6.0 | 6.2 |
| 2.5 mm or more to less than 5 mm | 9.1 | 8.3 |
| Less than 2.5 mm | 14 | 11.6 |

Table 1 indicates that the average brightness of the gingiva ultrasonic image has a negative correlation with the all teeth pocket depth in the oral cavity at a significance level of less than 5%. Thus, the all teeth average pocket depth of a subject can be determined by measuring the average brightness of an ultrasonic image of the attached gingiva of the subject and substituting the average brightness into a statistically derived statistical regression formula of the average brightness of an ultrasonic image of the attached gingiva and the all teeth average pocket depth. The all teeth average pocket depth of the subject can also be estimated by comparing the average brightness of the subject with the average brightness of which correlation with the all teeth average pocket depth is known. In addition, the all teeth average pocket depth of the subject can be estimated even more accurately by comparing the average brightness of the subject with the average brightness of which relation with the all teeth average pocket depth is known and which is close in health information (for example, smoking history) with. The possibility that the subject is affected by diseases such as gingivitis or periodontitis can be determined from the all teeth average pocket depth of the subject obtained from the gingival ultrasonic image, without professional diagnosis.

Comparative Example 2: Correlation of Average Brightness of Ultrasonic Image in Attached Gingiva Area and Alveolar Mucosa Area For the same subjects as in Example 3, the all teeth average pocket depth for each subject was calculated by a method similar to Example 3.

For each subject, the average brightness was calculated in the ranges from immediately below the epithelium to 500 μm below the epithelium and from immediately below the epithelium to 1500 μm below the epithelium in an ultrasonic image acquired from the alveolar mucosa area about 7 mm above the mucogingival junction closest to the interdental papilla of Upper Left/Right #1 to #5, by the method in Example 1. The analysis result is illustrated in Table 2 below.

TABLE 2

| All teeth average pocket depth | Attached gingiva (Example 3) Average brightness below gingival epithelium | | Alveolar mucosa (Comparative Example 2) Average brightness below gingival epithelium | |
|---|---|---|---|---|
| | From immediately below epithelium to 500 μm below epithelium | From immediately below epithelium to 1500 μm below epithelium | From immediately below epithelium to 500 μm below epithelium | From immediately below epithelium to 1500 μm below epithelium |
| 5 mm or more | 6.0 | 6.2 | 5.8 | 5.8 |
| 2.5 mm or more to less than 5 mm | 9.1 | 8.3 | 7.2 | 7.4 |
| Less than 2.5 mm | 14 | 11.6 | 7.1 | 7.2 |

According to Table 2, it has been found that the average brightness in the attached gingiva has a negative correlation with the all teeth average pocket depth of the subject at a significance level of less than 5%, in both of the range from immediately below the epithelium to 500 μm below the epithelium and the range from immediately below the epithelium to 1500 μm below the epithelium. On the other hand, it has been found that the average brightness in the alveolar mucosa area exhibits no significance correlation with the all teeth average pocket depth of the subject in either the range from immediately below the epithelium to 500 μm below the epithelium and the range from immediately below the epithelium to 1500 μm below the epithelium. It has been found that in order to predict the indicator of the all teeth average pocket depth of a person from an ultrasonic image, the ultrasonic image need to be acquired from the attached gingiva area.

Example 4: Study on Diameter of Measurement Probe

For the same subjects as in Example 3, the all teeth average pocket depth of each subject was calculated by a method similar to Example 3.

For each subject, an ultrasonic image of the attached gingiva area of the interdental papilla of Upper Left/Right #1 to #5 was acquired so as to include the interdental papilla attached gingiva, using a circular probe having a tip end with a diameter of 1 cm in contact with a test site, by the same method as Example 1. In the acquired ultrasonic image, the average brightness was calculated in the ranges from immediately below the epithelium to 500 μm below the epithelium and from immediately below the epithelium to 1500 μm below the epithelium. The analysis result is shown in Table 3 below together with the result in Example 4.

TABLE 3

| All teeth average pocket depth | In measurement with 2-mm φ Average brightness below epithelium (Example 3) | | In measurement with 1-mm φ Average brightness below epithelium (Example 4) | |
|---|---|---|---|---|
| | From immediately below epithelium to 500 μm below epithelium | From immediately below epithelium to 1500 μm below epithelium | From immediately below epithelium to 500 μm below epithelium | From immediately below epithelium to 1500 μm below epithelium |
| 5 mm or more | 6.0 | 6.2 | 6.2 | 5.8 |
| 2.5 mm or more to less than 5 mm | 9.1 | 8.3 | 7.2 | 6.5 |
| Less than 2.5 mm | 14 | 11.6 | 8.0 | 6.7 |

Table 3 indicates that the average brightness of the ultrasonic image acquired using a probe having a tip end with a diameter of 2 mm in contact with a test site has a negative correlation with the all teeth average pocket depth of the subject at a significance level of less than 5%, in both of the range from immediately below the epithelium to 500 μm below the epithelium and the range from immediately below the epithelium to 1500 μm below the epithelium. On the other hand, the average brightness of the ultrasonic image acquired using a probe having a tip end with a diameter of 1 cm in contact with a test site has a negative correlation with the all teeth average pocket depth of the subject in both of the range from immediately below the epithelium to 500 μm below the epithelium and the range from immediately below the epithelium to 1500 μm below the epithelium. However, when compared with the result in Example 3, using a probe with a diameter of 2 mm provides a more accurate indicator.

Example 5: Correlation Between Mobility of Adjacent Teeth of Subject and Average Brightness of Ultrasonic Image (Estimation of Periodontium State)

The periodontium is tissue connecting the teeth with the alveolar bone. When the periodontal function deteriorates due to progression of periodontal disease, injury, and other reasons, tooth movement is observed (Ten Cate's Oral Histology). For 40 men between the age of 55 to 60, one dental hygienist measured the mobility of four maxillary incisors using a Periotest (manufactured by Medizintechnik Gulden (manufacturer)).

For each subject, an ultrasonic image of the attached gingiva between maxillary incisors (at three points between Upper Left/Right #1 and #2 and between Upper Right #1 and Upper Left #1) in the range from immediately below gingival epithelium to 500 μm below the epithelium was acquired. In the acquired ultrasonic image, the average brightness was calculated for each measurement point in accordance with the method in Example 1, and the correlation between the average brightness of the attached gingiva at each measurement point and the mobility of teeth on both sides (Periotest measurement value) was analyzed. The evaluation result is illustrated in Table 4 below.

TABLE 4

| Mobility (Periotest measurement value) | Average brightness from immediately below epithelium to 500 μm below epithelium |
|---|---|
| 6 or more | 7.8 |
| 3 or more and less than 6 | 9.2 |
| 0 or more and less than 3 | 11.8 |
| less than 0 (minus) | 14.0 |

Table 4 indicates that the average brightness in the range immediately below the gingival epithelium to 500 μm below the epithelium has a negative correlation with the mobility of teeth on both sides at a significance level of less than 5%. The stronger the mobility, the higher the value of the Periotest. Thus, the tooth mobility of the subject can be estimated by measuring the average brightness of an ultrasonic image of the attached gingiva of the subject and substituting the average brightness into a statistically derived statistical regression formula of the average brightness of an ultrasonic image of the attached gingiva and the average mobility of teeth on both sides. The all teeth average pocket depth of the subject can also be estimated by comparing the average brightness of the subject with the average brightness of which relation with the tooth mobility is known. In addition, the all teeth average pocket depth of the subject can be estimated even more accurately by comparing the average brightness of the subject with the average brightness of which relation with the mobility is known and which is close in health information. The information on the tooth mobility of the subject therefore can be estimated without relying on professionals or uncomfortable diagnosis using a special device.

Example 6: Verification of Effect of Gum Care Product 2 groups were formed, each consisting of Five men between the age of 50 to 59. A group using an anti-periodontal disease dentifrice twice a day for three months was Group A, and a group using a control dentifrice was Group B. The composition of the dentifrice used by the subjects in each group is illustrated in Table 5 below.

TABLE 5

| Ingredients | Anti-periodontal disease dentifrice Content (%) | Control dentifrice |
|---|---|---|
| Sodium fluoride | 0.21 | 0.21 |
| Tranexamic acid | 0.05 | 0 |
| Vitamin E | 0.1 | 0 |
| Precipitated silica | 12.0 | 12.0 |
| 70% Sorbitol solution | 45.0 | 45.0 |
| Propylene glycol | 3.0 | 3.0 |
| Carboxymethyl cellulose | 0.8 | 0.8 |
| Carrageenan | 0.6 | 0.6 |
| Saccharin sodium | 0.18 | 0.18 |
| Sodium lauryl sulfate | 1.5 | 1.5 |
| Silicic acid anhydride | 4.0 | 4.0 |
| Flavor | 1.3 | 1.3 |
| Purified water | Balance | Balance |
| Total | 100 | 100 |

At the start of use and three months after the start of testing, a comprehensive examination for swelling, redness, and inflammation states of gingiva in the entire oral cavity was carried out by one dental hygienist, and the gingival average brightness of each subject was calculated by the method in Example 1. The effect of each dentifrice on the gingival state and the average brightness of the attached gingiva was analyzed. The same dental hygienist conducted the examination for all the subjects both at the start of the test and three months after the start of testing. This testing was blind, and the dental hygienist carried out the examination without knowing which of Group A and Group B each subject belonged to. The result of the examination of the gingival state by the dental hygienist is illustrated in Table 6 below.

TABLE 6

| | Group A | Group B |
|---|---|---|
| Significantly improved | 3 persons | None |
| Slightly improved | 1 person | 1 person |
| Not changed | 1 person | 3 persons |
| Deteriorated | None | 1 person |

Table 6 indicates that the gingival state-improving effect is higher in Group A. In the analysis of the ultrasonic images, in Group A, the average brightness of the attached gingiva in the range from immediately below the epithelium to 500 μm below the epithelium increases by 1, whereas in Group B, the average brightness decreases by 0.1. The average brightness of the attached gingiva obtained from an ultrasonic image of the attached gingiva is therefore also effective in evaluating the improving effect of dentifrice on the gingival constituents.

Example 7: Evaluation of Bleeding on Probing (BOP) Positive Ratio, Periodontal Inflamed Surface Area (PISA), and Periodontal Epithelial Surface Area (PESA)

For 200 subjects (men between the age of 30 to 72), five dental hygienists calculated the periodontal pocket depths of all the teeth by the six-point method, the bleeding on probing (BOP) positive ratio, and the periodontal inflamed surface area (PISA) and the periodontal epithelial surface area (PESA) calculated by the pocket depth and the positive ratio. For the 200 subjects, the average brightness of the attached gingiva of the interdental papilla of Upper Left/Right #1 to #2 in the range from immediately below the epithelium to 1500 μm below the epithelium was calculated by the method in Example 1. The correlation of the average brightness of each subject with the periodontal epithelial surface area (PESA), the bleeding on probing (BOP) positive ratio, and the periodontal inflamed surface area (PISA) by five dental hygienists was analyzed. The result of the statistical analysis is illustrated in Table 7 below.

TABLE 7

|  | r value | Spearman correlation analysis p value |
|---|---|---|
| Bleeding on probing (BOP) positive ratio | −0.2 | <0.05 |
| Periodontal inflamed surface area (PISA) | −0.2 | <0.05 |
| Periodontal epithelial surface area (PESA) | −0.3 | <0.01 |

According to Table 7, the average brightness of the image of the inside of the attached gingiva of a subject has a negative correlation with the periodontal epithelial surface area (PESA), the bleeding on probing (BOP) positive ratio, and the periodontal inflamed surface area (PISA). The higher the average brightness, the lower the bleeding on probing (BOP) positive ratio, the smaller the periodontal inflamed surface area (PISA), and the smaller the periodontal epithelial surface area (PESA). Thus, PESA, BOP positive ratio, and PISA of a subject can be estimated by measuring the average brightness of an ultrasonic image of the attached gingiva of the subject and substituting the average brightness into a statistically derived statistical regression formula of the average brightness of an ultrasonic image of the attached gingiva area and each evaluation item. PESA, BOP positive ratio, and PISA of a subject can also be estimated by comparing the average brightness of the subject with the average brightness of which relation with each evaluation item is known. In addition, PESA, BOP positive ratio, and PISA of a subject can be estimated even more accurately by comparing the average brightness of the subject with the average brightness of which relation with each of these indicator is known and which is close in health information. The information on PESA, BOP positive ratio, and PISA of a subject therefore can be estimated without relying on professionals or a diagnosis using a special device that may involve discomfort.

The invention claimed is:

1. A testing method for determining an oral indicator, the testing method comprising:
    acquiring an ultrasonic image of an inside of an attached gingiva of a subject, using a measurement probe;
    acquiring average brightness of a region of the inside of the attached gingiva in the ultrasonic image; and
    determining the oral indicator of the subject by referring to the average brightness and a reference of the oral indicator,
    wherein the region of the inside of the attached gingiva is a range from immediately below an epithelium up to 1500 um below the epithelium, and an acquisition range of the ultrasonic image has an area of 0.01 mm$^2$ to 20 mm$^2$.

2. The testing method according to claim 1, wherein a tip end of the measurement probe for measuring a surface of the attached gingiva has a diameter of 0.1 to 5 mm.

3. The testing method according to claim 1, wherein the the ultrasonic image is acquired with ultrasound having a radiation wavelength of 10 to 50 MHz.

4. The testing method according to claim 1, wherein the reference is previously-acquired average brightness associated with the oral indicator.

5. The testing method according to claim 1, wherein the reference is a statistical regression formula of the oral indicator.

6. The testing method according to claim 1, wherein the oral indicator is one or more of all teeth average pocket depth, amount of gingival collagen, gingival age, an indicator related to a state of the gingiva, an indicator of a symptom of the gingiva, bleeding on probing (BOP) positive ratio, periodontal inflamed surface area (PISA), and periodontal epithelial surface area (PEA).

7. A method of evaluating a gum care product, the method comprising:
    using a measurement probe, acquiring an ultrasonic image of an inside of an attached gingiva of a subject before using a gum care product and an ultrasonic image of the inside of the attached gingiva of the subject after using the gum care product;
    acquiring average brightnesses of a region of the inside of the attached gingiva from the ultrasonic images before and after using the gum care product, respectively; and
    determining that the gum care product is effective for gingival constituents when the average brightness after using the gum care product increases from the average brightness before using the gum care product, and determining that the gum care product is not effective for gingival constituents when the average brightness after using the Lim care product decreases from the average brightness before using the gum care product,
    wherein the region of the inside of the attached gingiva is a range from immediately below an epithelium to 1500 um below the epithelium, and an acquisition range of the ultrasonic images has an area of 0.01 mm$^2$ to 20 mm$^2$.

8. A method of selecting a gum care method, the method comprising:
    using a measurement probe, acquiring ultrasonic images of an inside of an attached gingiva of a subject before and after gum care, for each kind of gum care;
    acquiring an average brightness of a region of the inside of the attached gingiva change before and after care for each kind of gum care, from the ultrasonic images; and selecting a gum care method with the average brightness increase before and after care among the average brightness changes before and after care for each kind of gum care, wherein the region of the inside of the attached gingiva is a range from immediately below an epithelium to 1500 um below the epithelium, and an acquisition range of the ultrasonic images has an area of 0.01 mm$^2$ to 20 mm$^2$.

9. An oral indicator determining device comprising:

an ultrasonic image probe configured to acquire an ultrasonic image of an inside of an attached gingiva of a subject; and an image processing software configured to analyze the ultrasonic image, the image processing software configured to calculate average brightness of the inside of the attached gingiva from the ultrasonic image, and a determination unit configured to determine an oral indicator by referring to the average brightness and a reference of the oral indicator, wherein a region of the inside of the attached gingiva is a range from immediately below an epithelium up to 1500 um below the epithelium, and an acquisition range of the ultrasonic image has an area of 0.01 mm$^2$ to 20 mm$^2$.

10. The oral indicator determining device according to claim 9, wherein a tip end of the ultrasonic image probe for measuring a surface of the attached gingiva has a diameter of 0.1 to 5 mm.

11. The oral indicator determining device according to claim 9, wherein the ultrasonic image is acquired with ultrasound having a radiation wavelength of 10 to 50 MHz.

12. The oral indicator determining device according to claim 9, wherein the reference is already-acquired average brightness associated with the oral indicator.

13. The oral indicator determining device according to claim 9, wherein the reference is a statistical regression formula of the oral indicator.

* * * * *